United States Patent
Zawadzki et al.

(10) Patent No.: US 6,837,248 B2
(45) Date of Patent: Jan. 4, 2005

(54) REDUCED IGNITION PROPENSITY SMOKING ARTICLE

(75) Inventors: Michael A. Zawadzki, Greensboro, NC (US); Arthur M. Ihrig, Greensboro, NC (US); David A. Grider, Greensboro, NC (US); Terry D. Jessup, Jamestown, NC (US); David L. Williams, Greensboro, NC (US)

(73) Assignee: Lorillard Licensing Company, LLC, Greensboro, NC (US)

(*) Notice: Subject to any disclaimer, the term of this patent is extended or adjusted under 35 U.S.C. 154(b) by 0 days.

(21) Appl. No.: 10/402,651

(22) Filed: Mar. 28, 2003

(65) Prior Publication Data

US 2003/0164173 A1 Sep. 4, 2003

Related U.S. Application Data

(63) Continuation of application No. 09/795,054, filed on Feb. 26, 2001, now abandoned.

(51) Int. Cl.[7] ................................................. A24D 1/02
(52) U.S. Cl. ........................................ 131/365; 131/349
(58) Field of Search ........................... 131/360, 365; 162/139

(56) References Cited

U.S. PATENT DOCUMENTS

| | | | |
|---|---|---|---|
| 1,996,002 A | 3/1935 | Seaman | 131/52 |
| 2,013,508 A | 9/1935 | Seaman | 131/52 |
| 2,216,845 A | 10/1940 | Larson | 92/21 |
| 3,911,932 A | 10/1975 | Houch, Jr. et al. | 131/15 B |
| 4,077,414 A | 3/1978 | Baker et al. | 131/8 R |
| 4,129,134 A | 12/1978 | Hind et al. | 131/2 |
| 4,236,532 A | 12/1980 | Schweizer et al. | 131/9 |
| 4,420,002 A | 12/1983 | Cline | 131/334 |
| 4,450,847 A | 5/1984 | Owens | 131/365 |
| 4,452,259 A | 6/1984 | Norman et al. | 131/349 |
| 4,453,553 A | 6/1984 | Cohn | 131/365 |
| 4,506,684 A | 3/1985 | Keritsis | 131/369 |
| 4,615,345 A | 10/1986 | Durocher | 131/365 |
| 4,619,278 A | 10/1986 | Smeed et al. | 131/284 |
| 4,622,983 A | 11/1986 | Mathews et al. | 131/365 |
| 4,679,575 A | 7/1987 | Yamaguchi et al. | 131/365 |
| 4,730,628 A | 3/1988 | Townsend et al. | 131/264 |

(List continued on next page.)

FOREIGN PATENT DOCUMENTS

| | | | | |
|---|---|---|---|---|
| EP | 0 403 129 | | 12/1990 | A24D/1/02 |
| EP | 0 486 213 B1 | | 5/1992 | A24D/1/02 |
| EP | 0 870 437 B1 | | 10/1998 | A24D/1/02 |

OTHER PUBLICATIONS

Meier, B., Philip Morris Says It Has A Safer Paper—Trying To Cut Risk Of Cigarette Fires, The New York Times: p. 20, Column 1, Jan. 11, 2000.

(List continued on next page.)

*Primary Examiner*—Dionne A. Walls
(74) *Attorney, Agent, or Firm*—Morgan & Finnegan, L.L.P.

(57) ABSTRACT

A smoking article having reduced ignition propensity is disclosed. The smoking article includes a tobacco column, a wrapper surrounding the tobacco column and a filter element. The wrapper has a base permeability, an untreated area and a least one discrete area treated with a composition to reducing the base permeability. The discretely treated area interacts with a coal of a burning tobacco firecone as it advances to self-extinguish the smoking article. The composition of the treated area includes a permeability reducing substance, a burn rate retarding substance and a burn rate accelerating substance. Either the burn rate retarding substance or the burn rate accelerating substance acts as an organoleptic enhancing substance. In this way a smoker's experience when smoking either the at least one treated area or the untreated area is substantially the same.

60 Claims, 4 Drawing Sheets

U.S. PATENT DOCUMENTS

| | | | |
|---|---|---|---|
| 4,784,163 A | 11/1988 | Adams et al. | 131/284 |
| 4,889,145 A | 12/1989 | Adams et al. | 131/365 |
| 4,964,427 A | 10/1990 | Case et al. | 131/365 |
| 5,060,674 A | 10/1991 | Brown et al. | 131/365 |
| 5,060,675 A | 10/1991 | Milford et al. | 131/365 |
| 5,062,434 A | 11/1991 | Aulbach et al. | 131/336 |
| 5,103,844 A | 4/1992 | Hayden et al. | 131/365 |
| 5,143,098 A | 9/1992 | Rogers et al. | |
| 5,152,304 A | 10/1992 | Bokelman et al. | 131/365 |
| 5,154,191 A | 10/1992 | Owens, Jr. | 131/365 |
| 5,170,807 A | 12/1992 | Kasbo et al. | 131/365 |
| 5,191,906 A | 3/1993 | Myracle, Jr. | |
| 5,247,950 A | 9/1993 | Martin et al. | 131/365 |
| 5,263,500 A | 11/1993 | Baldwin et al. | 131/365 |
| 5,263,999 A | 11/1993 | Baldwin et al. | 131/365 |
| 5,332,472 A | 7/1994 | Cutright et al. | 162/139 |
| 5,342,484 A | 8/1994 | Cutright et al. | 162/139 |
| 5,360,516 A | 11/1994 | Cutright et al. | 162/139 |
| 5,417,228 A | 5/1995 | Baldwin et al. | |
| 5,450,862 A | 9/1995 | Baldwin et al. | 131/365 |
| 5,450,863 A | 9/1995 | Collins et al. | 131/365 |
| 5,474,095 A | 12/1995 | Allen et al. | 131/365 |
| 5,534,114 A | 7/1996 | Cutright et al. | 162/139 |
| 5,820,998 A | 10/1998 | Hotaling et al. | 428/533 |
| 5,849,153 A | 12/1998 | Ishino et al. | 162/135 |
| 5,878,753 A | 3/1999 | Peterson et al. | 131/365 |
| 5,878,754 A | 3/1999 | Peterson et al. | 131/365 |
| 5,966,218 A | 10/1999 | Bokelman et al. | |
| 5,997,691 A | 12/1999 | Gautam et al. | 162/134 |
| 6,020,969 A | 2/2000 | Struckhoff et al. | |

OTHER PUBLICATIONS

Wollenberg, S, Philip Morris To Use New Paper, AP Online, Jul. 11, 2000.

U.S. Borax Inc. Material Safety Data Sheet for Granubor® 1996.

Ecusta Corporation Porosity Conversion Table, Sep. 15, 1986.

Search Report issued in EP 1 213 514 A3, which is the EP counterpart application claiming priority to the parent US application (U.S. Appl. No. 09/795,054 filed Feb. 26, 2001) of the above–referenced application U.S. Appl. No. 10/402, 651 filed Mar. 28, 2003.

Test Methods for Quantifying the Propensity of Cigarettes to Ignite Soft Furniture; U.S. Dept. of Commerce, Ayg. 1993.

Quantifying the Ignition Propensity of Cigarettes; Fire & Materials, vol. 19, 155–169; Aug. 27, 1995.

Relative Ignition Propensity of Test Market Cigarettes; Richard G. Gann et al., National Institute of Standards and Technology; Jan. 2001.

Ecutsa Corporation brochure, Porosity Conversion, Sep. 15, 1986, p. 2, document No. 1002815709.

Kimberly–Clark Corporation brochure, Cigarette Paper Porosity Conversion charts, Jun. 1976, document No. 88043332.

Arthur M. Ihrig and Sheryl L. Smith, The Role of Alkali and Alkaline Earth Metal Ions in Cellulosic Smoldering: Journal of Fire Sciences vol. 12, Jul./Aug. 1994, pp. 357–375; (presented in part at the $46_{th}$ Tobacco Chemist Research Conference, Montreal, Canada Sep. 27–30, 1992).

William F. Owens, Jr., Effect of Cigarette Paper On Smoke Yield and Composisition, pp. 1–22; Recent Advances In Tobacco Science, vol. 4, pp. 3–24, $32_{nd}$ TCRC, 1978; (presented in part at the Technical Department, Ecusta Paper and Film Group, Olin Corporation, Pisgah Forest, North Carolina 28786 in 1978).

Dictionary of Tobacco Terms, Sep. 1999, which may be found at the following website: www.smoke–fee.ca/eng__research/pscresearch__papers.htm; (sources include the Dictionary of Tobacco Terminology, M.Z. Debardeleben (1987) Philip Morris document ID: 2054432502/2628; Glossary/Acronyms List, C.S. Lincoln (1987); Brown & Williamson document, pp. 620411092–620411135; and Proceedings of the Smoking Behavior—Marketing Conference 84709–840712 (1984), B&W document ID 588065; RJR document ID 511331024–1028 dated 1993).

A.S. Dixit; R.H. Martin; W.F. Owens; Ecusta, Cigarette Paper Properties That Influence Sidestream Smoke Delivery, 1991, pp. 507931499–507931507; (presented at the $45^{th}$ Tobacco Chemist's Research Conference, Oct. 20–23, 1991, Grove Park Inn, Ashville, North Carolina).

Arthur M. Ihrig and Shirley Smith, The Effects of Ions on Cigarette–Initiated Smoldering Ignitions of Cellulosic Fabrics, 1992, pp. 1–16; (presented at the $46^{th}$ Tobacco Chemist Research Conference, held i n Montreal, Canada, Sep. 27–30, 1992).

Arthur Ihrig; Michael Zawadzki; and Dave Grider, Some Critical Parameters and their Effect on Cigarette Ignition Propensity, Jan. 8, 2001; (presented at the $32^{nd}$ International Conference on Fire Safety on Jan. 8, 2001 at The Greenbrier in White Sulphur Springs, West Virginia).

REDUCED IGNITION PROPENSITY SMOKING ARTICLE

This application is a continuation of application Ser. No. 09/795,054, filed Feb. 26, 2001, now abandoned.

BACKGROUND OF THE INVENTION

The present invention relates generally to a wrapper for a smoking article to create a reduced ignition propensity (IP) smoking article and, more particularly, to a smoking article having the ability to freeburn in a static state and reduced IP. Under some circumstances cigarettes may ignite fire-prone substrates if the article is laid or accidentally contacts the substrate. Therefore, a cigarette prepared from a wrapper, which diminishes the ability of the article to ignite a substrate, may have the desirable effect of reducing cigarette-initiated fires. Furthermore, a wrapper that concurrently confers on the cigarette the ability to freeburn in a static state and reduced IP character allows a beneficial reduction in the tendency of the article to ignite fire-prone substrates while maintaining consumer acceptability.

There have been various attempts to create a cigarette that has reduced IP and consumer acceptable attributes particularly taste and the ability to freeburn in the static state. Technologies that appear to provide such cigarettes are described in the patent literature. Cigarettes claiming to possess reduced IP are commercially available.

A factor that manufacturers consider in preparing a smoking article having reduced IP is whether currently used processes and equipment will remain substantially unchanged. One method for preparing a reduced IP paper involves the addition of elaborate equipment on a conventional papermaking machine. Cellulose fibers or particles suspended in water are sprayed from angular moving nozzles moving at an angle to a continuous forming moist web. This approach involves the coordinated angular movement of the spray nozzle and the about 400 feet per minute moving web to create spaced apart bands transverse to the web. The above-mentioned technology suffers from a number of deficiencies that limit consumer acceptability, IP reduction, and ease of manufacture. The technology requires expensive add-on equipment including a spray nozzle system and an associated slurry distribution system, pressure regulating system, and a means for carefully synchronizing the angular material distribution system with the underlying papermaking machine.

The reduced consumer acceptable properties of the prepared cigarettes are due to factors including reduced ability of the cigarette to freeburn in the static state, poor ash appearance, and variable taste profile.

The poor IP reduction performance achieved by cigarettes prepared with wrappers made using this technology is believed to be caused by a number of factors including difficulty in depositing an even layer of the cellulose fibers or particles, low efficiency of the cellulose fibers or particles to reduce the permeability of the underlying web, and poor reproducibility caused by fanning out of the sprayed material. Deficiencies in the approach that limit ease of manufacture include the difficulty in synchronizing the angular moving cellulose fibers and particles distribution apparatus with the underlying web forming apparatus and difficulty in reducing the banded moist web to dryness without disrupting the structure of the web.

Another technology involves adding discrete material regions to the dry web using organic solvent-based printing equipment. Organic solvents and non-aqueous soluble solutes are used to make the discrete regions on the web. The presence of organic solvents requires hoods to capture the solvent vapors and the corresponding further expenses.

In regard to commercially available cigarettes claiming to possess reduced IP, consumers may find their organoleptic experience wanting. Some technologies that are based on discretely treated areas for reduced IP cigarettes create a varying organoleptic experience as the consumption of the smoking article moves from treated area to non-treated areas.

One commercial product claiming to possess reduced IP is characterized by a tendency to extinguish when left burning in the static state—that is reduced freeburn. The article displays a less desirable taste when relit after being extinguished. Thus, although the cigarette may possess the reduced IP, the reduced freeburn property decreases consumer acceptability of the article.

Other factors affecting consumer acceptability are product appearance, including pleasing and consistent wrapper and ash character. Moreover, it is important that the construction of the smoking article exhibit a reasonable shelf-life while maintaining reduced IP.

Thus, there remains a need for a new and improved wrapper and smoking article having reduced IP while at the same time possessing a sufficient free burn. Also, there remains a need for a new and improved method for making a wrapper that can be used to create a smoking article having reduced IP and sufficient freeburn.

SUMMARY OF THE INVENTION

The present invention is directed to a smoking article having reduced IP. The smoking article includes a tobacco column, a wrapper surrounding the tobacco column and, optionally, a filter element. The wrapper has a base permeability, an untreated area and a least one discrete area treated with a composition to reduce the base permeability. The discretely treated area interacts with a coal of a burning tobacco firecone as it advances to self-extinguish the smoking article if the smoking article is left on a surface or causes the cigarette not to ignite the surface.

The tendency of a cigarette to self-extinguish or not ignite surfaces can be measured by the use of IP tests such as those published by the Consumer Products Safety Commission and developed by the National Institute of Standards and Technology (NIST) or the American Society of Testing and Materials (ASTM). See Ohlemiller, T. J. et al., "Test Methods for Quantifying the Propensity of Cigarettes to Ignite Soft Furnishings. Volume 2, "NIST SP 851; volume 2; 166 pages [also includes: Cigarette Extinction Test Method, see pp. 153–160] August 1993 available from U.S. Consumer Product Safety Commission, Washington, D.C. 20207 as order number PB94-108644, the subject matter of which is herein incorporated by reference. One NIST IP test, the "cotton duck test", involves placing a smoldering cigarette on a test assembly composed of a cellulosic fabric over a foam block. Variations of the test use fabrics of various weights and polyethylene sheet backing. A test failure occurs when the fabric ignites. Another NIST IP test, the "filter paper test", involves placing a smoldering cigarette on a test assembly composed of layered filter paper sheets. Various forms of the test use 3, 10, and 15 layered filter paper sheets. A successful test result occurs when the cigarette self extinguishes before the whole tobacco column is consumed.

The composition of the treated area includes at least a permeability reducing substance. Another substance in the treated area includes a burn rate retarding substance. Yet another substance in the treated area includes a burn rate accelerating substance. Either the burn rate retarding substance or the burn rate accelerating substance or both preferably acts as an organoleptic enhancing substance. In this way a smoker's experience when smoking either the at least one treated area or the untreated area is substantially the same. Additionally, the composition of the treated area may include a filler component.

In a wrapper making process, the applied amount of the permeability reducing substance, the burn rate retarding substance, and the burn rate accelerating substance is such as to give the desired freeburn character and IP reduction to a finished article made from the wrapper. The quantity and the concentration of the applied composition will depend on factors including the absorbency of the web, polymer properties of the permeability reducing substance, whether the web is wet or dry, and the operating conditions of the application equipment.

The burn rate accelerating substance may be an alkali metal or alkaline-earth containing salt. Preferably, the burn rate accelerating substance may be an alkali metal salt of a carboxylic acid such as acetic acid, citric acid, malic acid, lactic acid, tartaric acid and the like. Preferably, the salt of the carboxylic acid is a salt of citric acid. Also, the alkali metal containing compound is preferably at least one of a sodium containing compound and a potassium containing compound. Alternatively, the burn rate accelerating substance may be monoammonium phosphate.

The burn rate retarding substance may be a phosphate, preferably a phosphate of ammonium and more preferably a diammonium phosphate.

The permeability reducing substance may be a pore filling substance, a film forming substance or combination thereof. The permeability reducing substance may be a polymer and, preferably, a polysaccharide. Among the contemplated polysaccharides are starch, including various mixtures of amylose, amylopectin and dextrin, modified starch and starch derivatives. The starch and starch derivatives may be water dispersible and, preferably, water soluble. Other contemplated polysaccharides include cellulose, cellulose derivatives, chitosan, chitosan derivatives, chitin, chitin derivatives, alginate, alginate derivatives and combinations thereof. These polysaccharides are preferably water dispersible and, more preferably, are water-soluble.

In one embodiment, the discretely treated area is a circumferential band about the body of the article. The band has a sufficient width so as to deprive the coal of the burning tobacco firecone of oxygen from behind a char line of the wrapper when the smoking article is placed on a surface. That may be achieved by a band width typically of at least about 3 millimeters.

In an alternative embodiment, the discretely treated area includes at least two bands spaced sufficiently to reduce the IP of the smoking article. In this case, the two bands preferably have a center-to-center spacing of between about 10 millimeters to about 30 millimeters. The two bands may have a width of about 3 millimeters to about 10 millimeters. A center-to-center spacing is preferably about 25 millimeters.

The discretely treated area preferably has a thickness and properties so a bobbin of the wrapper is useable in a commercially available smoking article manufacturing machine. Also, the discretely treated area is preferably visually substantially the same as the untreated area.

Still another aspect of the present invention is to provide a population of smoking articles having a reduced IP. Each smoking article within the population includes a tobacco column, wrapper surrounding the tobacco column so that the smoking article includes an ignition end and a distal end, and at least one banded region, preferably at least two spaced apart banded regions, between the ignition end and the distal end having a combustion characteristic substantially different from that of an non-banded, untreated, region. A distance from the ignition end to the at least one of the banded region of each smoking article may be sequentially related, random, or quasi-random within a selected population.

In one embodiment, the selected population is a package of smoking articles and in another embodiment a grab sample of smoking articles.

In another embodiment, the distance from the ignition end to the at least one of the banded regions of each smoking article are sequentially related, random, or quasi-random.

In a preferred embodiment, the IP of the selected population is between about 50 and about 100 percent for the population.

The invention also provides a method of making a wrapper, of making a smoking article having reduced IP, and a composition for application to a paper to make a wrapper and a smoking article.

BRIEF DESCRIPTION OF THE DRAWINGS

The invention will be better understood after a reading of the following description of the preferred embodiment when considered with the drawings in which.

DESCRIPTION OF THE PREFERRED EMBODIMENTS

Figure 1:
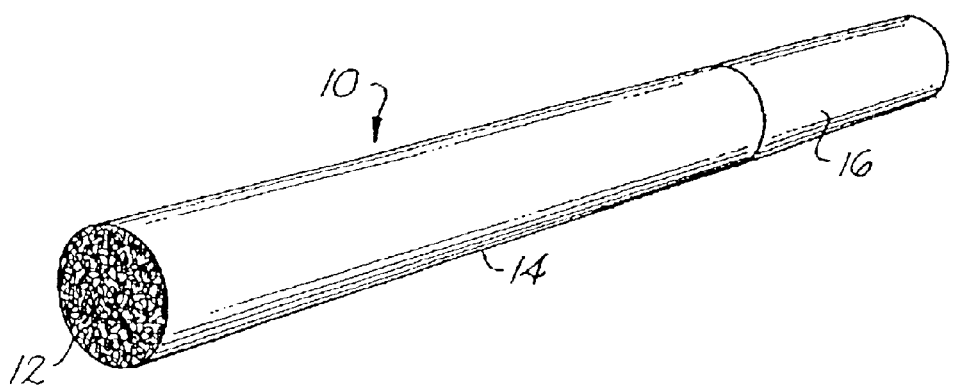
FIG. 1 is a perspective view of a smoking article according an embodiment of the present invention.

Referring now to the drawings in general and FIG. 1 in particular, it will be understood that the illustrations are for the purpose of describing a preferred embodiment of the invention and are not intended to limit the invention thereto. As best seen in FIG. 1, a smoking article 10 includes a tobacco column 12 surrounded by a wrapper 14. The smoking article 10 may, as an option, include a filter element 16 adjacent to the tobacco column 12 surrounded by the wrapper 14.

Figure 2:
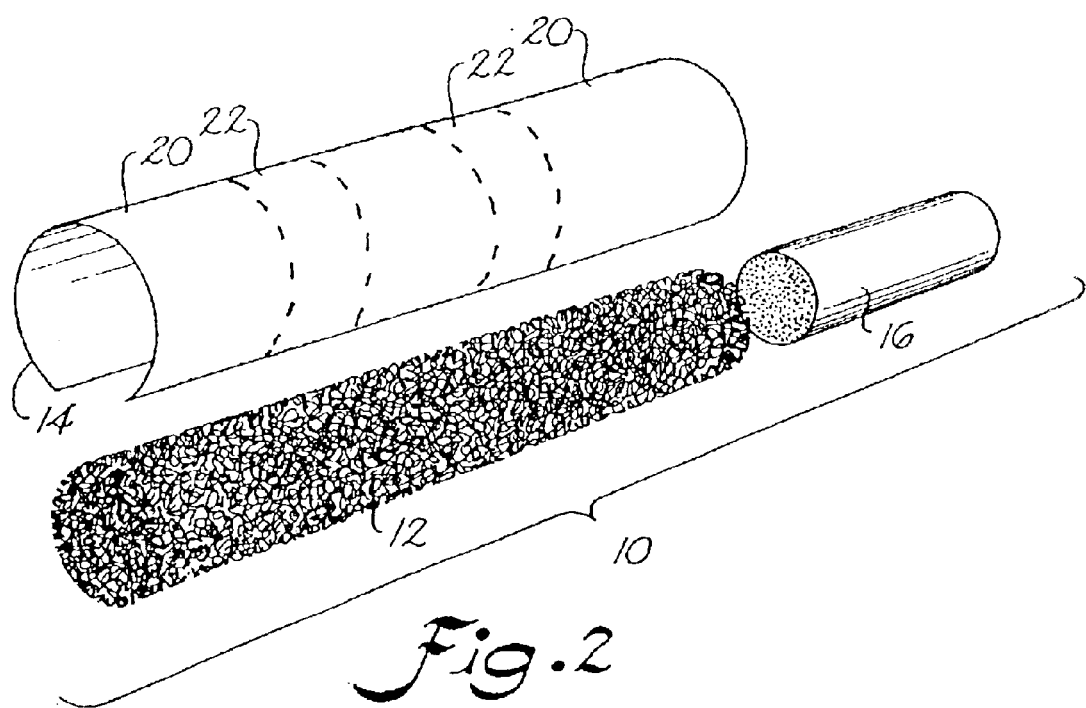
FIG. 2 is an exploded view of the smoking article of FIG. 1.
Figure 3:
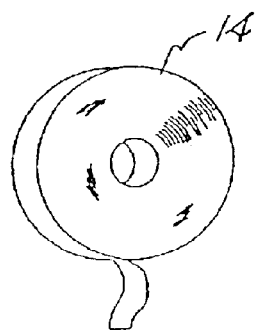
FIG. 3 is a perspective view of a bobbin of wrapper that may be used to make the smoking article of FIG. 1.
Figure 4:
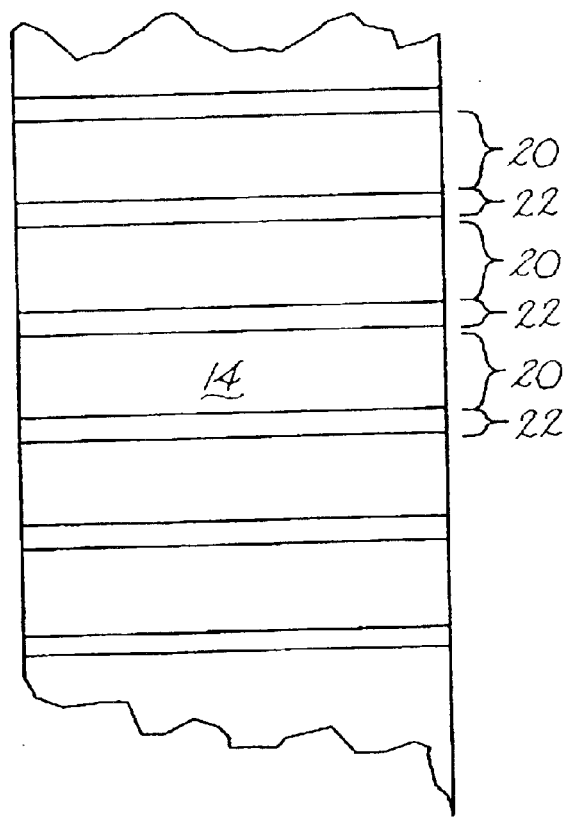
FIG. 4 is a plan view of a wrapper as might be accumulated in a bobbin as shown in FIG. 3.

FIG. 2 shows an exploded view of the smoking article 10 of FIG. 1 including certain aspects relating to the wrapper 14, which is a modified cigarette paper. In particular, wrapper 14 includes untreated areas 20 alternating with treated areas 22. Treated areas 22 include a combination of substances that interact with the wrapper 14 to create the reduced IP smoking article 10. At least one of the substances in treated area 22 includes a permeability reducing substance. Another substance in treated area 22 includes a burn rate retarding substance. Yet another substance in treated area 22 includes a burn rate accelerating substance. Optionally, another substance in the treated area includes filler. These substances interact with each other and the wrapper paper 14 to create a wrapper that may be used to manufacture reduced IP smoking article 10.

The permeability reducing substance may be a polymer. The polymer may be any one of a natural polymer, a derivative of a natural polymer, a synthetic polymer, and a combination of any of the preceding. Applicants have found that polysaccharides are suitable as permeability reducing substances. The polysaccharides may be at least one of a starch, modified starch, starch derivative, cellulose, cellulose derivative, chitosan, chitosan derivative, chitin, chitin derivative, alginate, alginate derivative or a combination of any of the preceding. Any polysaccharide that suitably reduces the permeability of the wrapper would be appropriate for use as the permeability reducing substance.

Applicants believe that starch, modified starch, starch derivatives, cellulose and cellulose derivatives would act particularly well as permeability reducing substances. Applicants have found that starch and starch derivatives work particularly well as the permeability reducing substance. Water soluble and water dispersible starch, starch derivatives, cellulose and cellulose derivatives would be more desirable than nonaqueous solvents and dispersants. Nonaqueous solvents may be harmful to workers, or environmentally regulated so that exhaust equipment that may be needed to capture organic solvent mists and vapors.

Without wishing to be bound by any scientific theory and explanation, applicants believe that a permeability reducing substance may interact with the wrapper in a number of ways. In one, a permeability reducing substance may form a film on the wrapper 14 to reduce permeability by blocking pores in the wrapper 14. That is, when the permeability reducing substance is applied to the wrapper 14, a film is created that acts as a barrier to block the movement of gas through pores in the discretely treated area 22.

Alternatively, a permeability reducing substance may act to fill pores and thereby reduce the porosity of the wrapper 14. In this way, a discretely treated area 22 possesses porosity or gas permeability less than that of the untreated area 20 of the wrapper 14.

As a further alternative, a permeability reducing substance may both form a film on the wrapper 14 and act to fill pores in the wrapper 14 so that a discretely treated area 22 possesses a porosity or gas permeability less than that of the untreated area 20 of the wrapper 14.

Applicants have determined that the permeability in the discretely treated area 22 of wrapper 14 may be less than about 10 CU (CORESTA units, $cm^3/min/cm^2$ at 1 kPa measuring pressure as substantially measured according to CORESTA [Cooperative Centre for Scientific Research Relative to Tobacco, Paris, France] Recommended Method No. 40: Determination of Air Permeability of Materials Used as Cigarette Paper, Filter Plug Wrap and Filter Joining Paper including Materials Having an Oriented Permeable Zone, October 1994, published in Bulletin 1994–3/4, the subject matter of which is incorporated herein by reference) and is preferably less than about 7 CU. Alternatively, the band area, and optionally untreated area, may contain a perforation zone produced by methods such as electrostatic and mechanical perforation and the like that are known to those skilled in the art. Applicants have discovered the unexpected property that a banded area, possessing a perforation zone, may exhibit a relatively high apparent permeability while still conferring a reduced IP character on an article made from the thus treated paper. In a preferred embodiment the permeability of a perforated band may be less than about 60 CU.

A burn rate retarding substance includes any substance that reduces the smolder rate of materials such as paper, cloth and plastic, and may also increase their resistance to flaming combustion. Phosphates have been found to work well and, in particular, phosphates of ammonium. A particular preferred phosphate of ammonium is the diammonium phosphate (having synonyms such as diammonium hydrogenphosphate; DAP; diammonium hydrogenorthophosphate; phosphoric acid, diammonium salt; and ammonium hydrogen phosphate).

A burn rate retarding substance may have additional beneficial benefits including unexpected improved organoleptic properties discovered by applicants. To that end, applicants have found that consumers detect a more pleasing smoke taste when the burn rate retarding substance is present in the discretely treated area 22 in smoking article 10 according to the present invention.

A burn rate retarding substance also may cooperate with a permeability reducing substance in another unexpected synergistic manner. That is, the inclusion of a burn rate retarding substance may reduce the amount of a permeability reducing substance that may need to be applied to a discretely treated area 22. This may have an impact on the manufacturability of a wrapper 14 according to the present invention by decreasing the amount of permeability reducing material needed to achieve IP reduction.

A burn rate accelerating substance includes any substance known to increase the rate at which the smolder process of such materials as paper, cloth and plastic takes place. Such a substance may contribute to the free burn of a smoking article 10 according to the present invention. Preferably, a reduced IP smoking article 10 self-extinguishes when placed onto a surface and continues to burn when the smoking article 10 is freely suspended such as within the holder of an ashtray or held without puffing. This latter attribute is known as "freeburn." To that end, a burn rate accelerating substance interacts with the wrapper 14, the permeability reducing substance, and the burn rate retarding substance to create a discretely treated area 22 that works to maintain the balance between self-extinguishment and freeburn.

A burn rate accelerating substance may be a salt such as an alkali metal and an alkaline-earth metal containing salt and, preferably, one containing an alkali metal preferably sodium, potassium and sodium and potassium. The salt may be a salt of a carboxylic acid such as acetic acid, citric acid, malic acid, lactic acid, tartaric acid and the like. In a particularly preferred embodiment, it is a salt of a citric acid. Alternatively, the burn rate accelerating substance may be monoammonium phosphate.

A burn rate accelerating substance may have additional beneficial benefits including unexpected organoleptic enhancing abilities discovered by applicants. To that end, applicants have found that consumers detect substantially no difference between smoking an untreated area 20 and a discretely treated area 22 in smoking article 10 according to the present invention. This removes the need for difficult to achieve gradations, such as described in U.S. Pat. No. 5,878,753, between a discretely treated area 22 and untreated areas 20 to maintain a substantially consistent organoleptic experience for the consumer.

A filler substance includes particulate materials such clay, chalk (calcium carbonate), and titanium oxide. Applicants believe that the presence of filler may be beneficial during the manufacture of discretely treated areas 22 by allowing the appearance, particularly the opacity, of discretely treated areas 22 to be carefully controlled so as to be substantially the same as the untreated region 20.

A manufacturing of discretely treated areas 22 may be made by applying compositions that are applicable to the wrapper 14 when the wrapper 14 might be in a wet or dry state or a semi-wet state. Those skilled in the art will appreciate that the quantity and the concentration of the applied composition will depend on factors including the absorbency of the web, properties of the permeability reducing substance, whether the web is wet or dry, and the operating conditions of the application equipment. Moreover, those skilled in the art will appreciate that the composition may be applied by a number of known methods including spraying, stenciling, flexographic printing, gravure printing, and the like including both multiple-pass and single-pass processes.

Preferably, the composition for affecting the discretely treated areas may be applied on one side of the base paper such that the formed band 22 faces the tobacco-side 12 after making article 10 from the banded paper. Alternatively, the composition may be applied on both sides of the paper or applied such that the formed band 22 faces the outside or consumer-side after making article 10 from the banded paper.

Figure 5A:
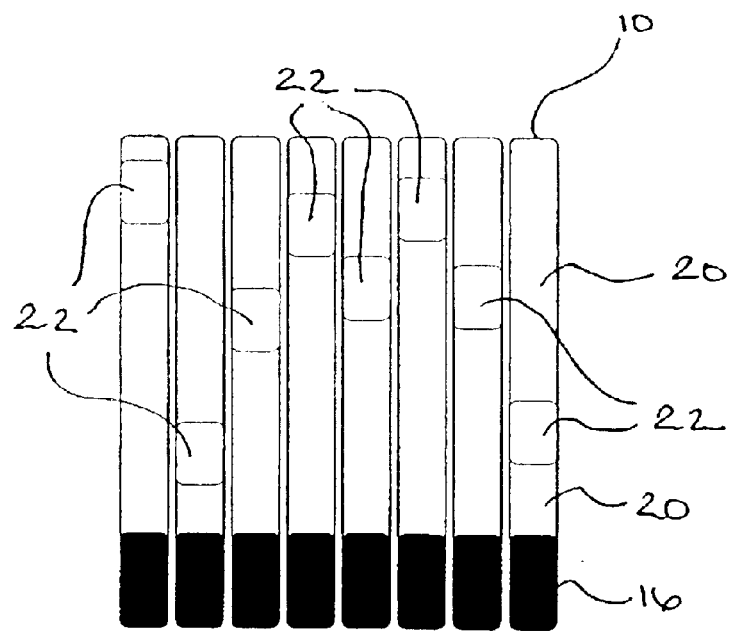
FIG. 5A is a schematic of a population of smoking articles having a substantially random distance from the ignition end to the at least one of the banded region of each smoking article within the population according an embodiment of the present invention.
Figure 5B:
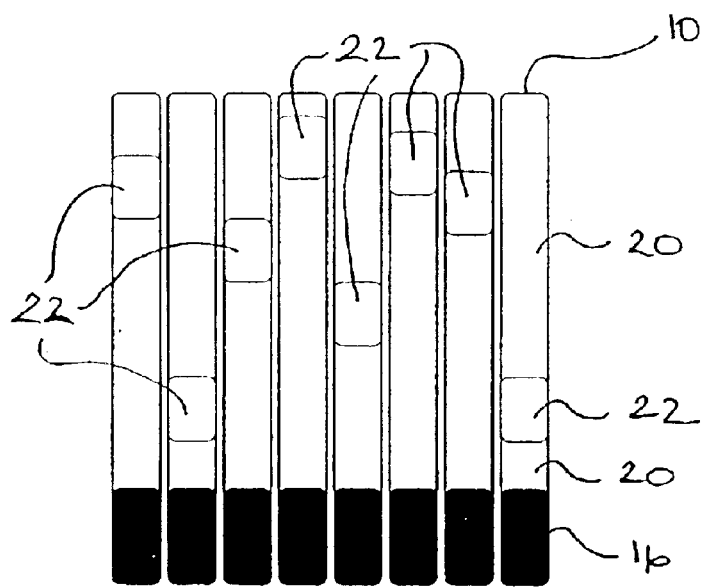
FIG. 5B is a schematic of a population of smoking articles having a quasi random distance from the ignition end to the at least one of the banded region of each smoking article within the population according an embodiment of the present invention.
Figure 5C:
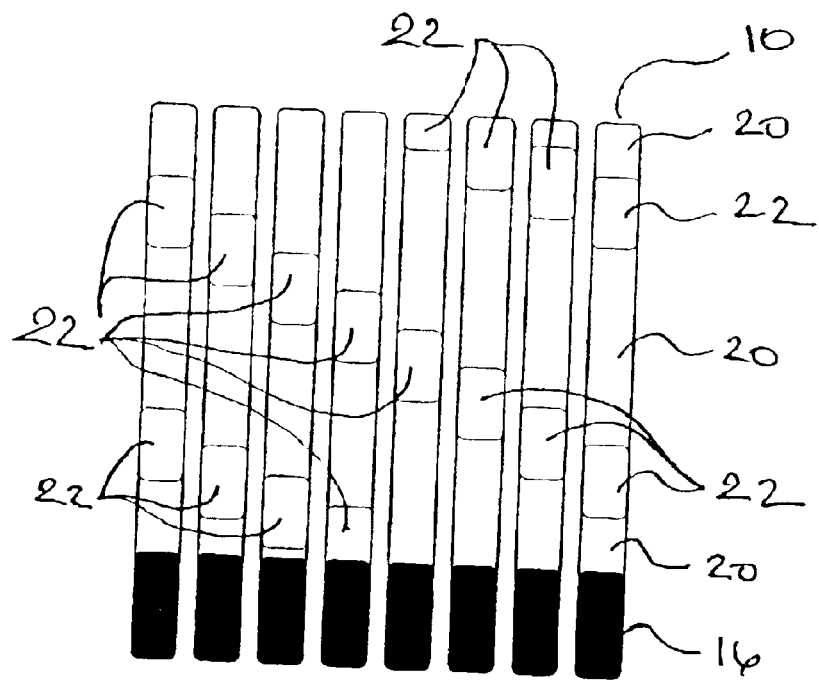
FIG. 5C is a schematic of a population of smoking articles having a sequentially related distance from the ignition end to the at least one of the banded region of each smoking article within the population according an embodiment of the present invention.
Figure 6:
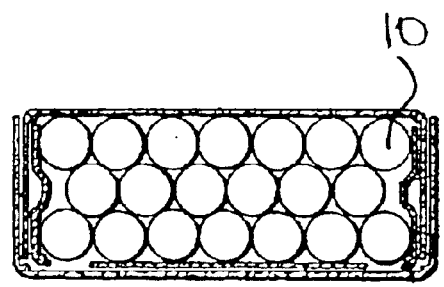
FIG. 6 is a schematic of a package of smoking articles of any of FIG. 1, FIG. 5A, FIG. 5B and FIG. 5C.

Manufacturing of reduced IP smoking articles is preferably accomplished using a reel, or bobbin, length of wrapper 14 with discretely treated areas 22 and untreated areas 20. Using a bobbin of banded paper in a cigarette-making machine will provide a population of banded smoking articles having a reduced IP. That is, each smoking article within the population will include a tobacco column, wrapper surrounding said tobacco column so that the smoking article includes an ignition end and a distal end, and at least one banded region, preferably at least two spaced apart banded regions, between the ignition end and the distal end whereby the distance from the ignition end to the at least one of the banded region of each smoking article may be random (substantially as depicted in FIG. 5A), quasi-random (substantially as depicted in FIG. 5B), or sequentially related (substantially as depicted in FIG. 5C) within the population. The population may any population such as a grab sample and a package of cigarettes as depicted in FIG. 6.

Applicants believe that the sequentially related, random, or quasi-random band position would have the benefit of allowing the cigarette population as a whole to have fewer tendencies to ignite fire-prone substrates. Overall, IP tests incorporate a fixed burn-down distance in which the article is burned before being placed on the test substrate. In real-world ignition scenarios the article may burn down to any distance with respect to the ignition end of the article before contacting a substrate. Therefore, a sequentially related, random, or quasi-random band position will increase the probability that any individual member of the banded article population may prevent ignition of a prone substrate when the article is burned down to a random distance before substrate contact. Alternatively, bands may be registered at a fixed distance with respect to the ignition end of article 10. The preferred embodiment of this invention is for the manufacture of reduced IP articles having a sequentially related, random, or quasi-random band position with respect to the ignition end of article 10.

The following examples relate to smoking articles produced according to the present invention and are provided to more fully explain the invention. In the examples describing sample cigarette papers made by "gravure printing" the samples were made using a single-pass gravure printing process. Bands on the gravure-printed paper were about 6 mm wide, substantially perpendicular to the paper edge, and applied at about 25 mm intervals center to center. After printing and allowing the applied composition to dry, the treated paper was slit and rolled into bobbin form compatible with a standard cigarette-making machine. The banding composition was printed on one side of the base paper such that band 22 was facing the tobacco-side 12 after making article 10 from the banded paper. Gravure print-banded paper was used to manufacture cigarette using a conventional cigarette-making machine thereby giving a selected population of cigarettes with quasi-random band positions.

In the examples describing sample cigarettes prepared by "hand banding" a circumferential ring of material was applied around the body of smoking article, by hand, using an aluminum printing plate. The aluminum printing plate was fashioned from a slab of aluminum metal with a straight channel, about 7 millimeters wide and about 30 millimeters long, milled below the surface of the slab. A banding composition was used to fill the channel of the printing plate. The smoking article was then rolled, by hand, across the composition-filled channel such that a circumferential band was formed about the body of the smoking article. Therefore, the about 7 millimeter wide band was printed on one side of the wrapper such that band 22 was on the outside or consumer-side of article 10. Hand banded cigarettes are characterized as having the applied band registered at a fixed position with respect to the ignition end of the article.

In each of the examples, "freeburn" was measured by igniting a cigarette and placing the smoldering article horizontally in a holder. The article was allowed to statically smolder without the column or ember contacting a surface. A positive freeburn result occurred when the cigarette was consumed to the filter element.

In each of the examples, a series of conventional flax pulp cigarette papers were used and the properties of these papers are given in Table 1.

TABLE 1

Average Base Paper Properties.

| Paper | Permeability (CU) | Filler (%)* | Citrate (%)** | Basis Weight (g/m$^2$) |
|---|---|---|---|---|
| A | 18 | 30 | 0.85 | 25.5 |
| B | 29 | 29 | 0.85 | 25.5 |
| D | 31 | 28 | 2.30 | 26.0 |
| E | 32 | 28 | 0.60 | 26.0 |
| F | 37 | 30 | 0.90 | 26.0 |
| G | 48 | 28 | 0.93 | 25.5 |
| H | 71 | 32 | 0.70 | 25.8 |

*Weight percent calcium carbonate
**Weight percent citrate salt

EXAMPLE 1

Three smoking article types were made using a paper wrapper, an about 63 millimeter tobacco column length, an about 21 millimeter cellulose acetate non-air diluted filter section, and a cigarette tobacco blend. The cigarettes were made on a conventional cigarette-making machine. Two of the smoking article samples were made using separately banded, reduced IP papers. The third smoking article sample served as a control and was made from a standard cigarette paper. For all smoking article samples in this example paper A was used.

Two banded wrappers were made by applying permeability reducing compositions on base paper A using gravure printing. About 60,000 cigarettes were made for each of a high band weight wrapper type, designated 1-C, a low band weight wrapper type, designated 1-B, and a conventional non-banded wrapper, designated 1-A, as a control. All cigarette types were tested for IP according to the NIST (10-sheet) filter paper IP test and freeburn.

Cigarette type 1-B was made from cigarette paper A gravure printed with a composition containing about 20.5 weight percent Flokote-64® starch (National Starch, Berkeley, Calif.), about 0.90 weight percent DAP (Rhodia, Cranbury, N.J.), about 8.40 weight percent citrate salt, and bout 70.17 weight percent tap water. The citrate salt was a mixture of sodium citrate dihydrate (Fisher Scientific, Fair Lawn, N.J.) and potassium citrate monohydrate (Fisher Scientific, Fair Lawn, N.J.) in an about 1:2.8 weight/weight ratio. The composition was heated at approximately 87° C. for about 15 minutes. The permeability in the banded region was measured as about 6 CU.

Cigarette type 1-C was made from cigarette paper A gravure printed with a composition containing about 27.21 weight percent Flokote-64® starch (National Starch, Berkeley, Calif.), about 1.20 weight percent DAP (Rhodia, Cranbury, N.J.), about 11.13 weight percent citrate salt, and about 60.46 weight percent tap water. The citrate salt was a mixture of sodium citrate dihydrate (Fisher Scientific, Fair Lawn, N.J.) and potassium citrate monohydrate (Fisher Scientific, Fair Lawn, N.J.) in an about 1:2.8 weight/weight ratio. The composition heated at approximately 87° C. for about 15 minutes. The permeability in the banded region was measured as about 4 CU.

During cigarette production, approximately 100 cigarettes were collected after about multiples of about 6,000 cigarettes were produced. The banded, reduced IP, papers ran substantially the same as the non-banded standard cigarette paper. No manufacturing or packing problems were observed.

Table 2 indicates IP and freeburn results for the control cigarette. The results in Table 3 and Table 4 indicate that the reduced IP prototypes cigarettes were characterized as having significant IP reduction, relative to the control, while maintaining the ability to freeburn in the static state.

Applicants observed that the manufacturing of cigarettes 1-B and 1-C gave a population of banded cigarettes. The band position of grab samples, collected on the cigarette-making machine immediately after manufacture, were believed to have sequentially related band positions. Overall, the band position relationship between the grab samples and the population as a whole was believed to be quasi-random. The results in Tables 2 and 3 show that the freeburn and IP reduction for the grab samples was similar to the population average.

The smoke taste profile of cigarettes 1-B and 1-C were substantially the same as control cigarette 1-A in terms of taste when smoking within banded areas and smoking in the untreated, non-banded, areas. The bands on 1-B and 1-C cigarettes were found to be nearly undetectable compared to the non-banded control article 1-A. For the reduced IP articles, 1-B and 1-C, the appearance of the ash after the banded region was smoked through was substantially the same as the ash formed when the untreated, non-banded, region was smoked through. Overall, the ash appearance of the reduced IP cigarettes, 1-B and 1-C was substantially the same as the control article 1-A.

TABLE 2

IP and Freeburn Results for Control Cigarette 1-A.

| IP Pass (%)* | Replicates | Freeburn (%) | Replicates |
|---|---|---|---|
| 0 | 8 | 100 | 32 |

*NIST (10-sheet) filter paper IP test

TABLE 3

IP and Freeburn Results for Samples of 1-B Acquired During A Manufacturing Trial.

| Grab Samples* | IP Pass (%)** | Replicates | Freeburn (%) | Replicates |
|---|---|---|---|---|
| B-1 | 87.5 | 8 | 100 | 8 |
| B-2 | 62.5 | 8 | 100 | 8 |
| B-3 | 75.0 | 8 | 100 | 8 |
| B-4 | 100 | 8 | 100 | 8 |
| B-5 | 87.5 | 8 | 100 | 8 |
| B-6 | 87.5 | 8 | 100 | 8 |
| B-7 | 62.5 | 8 | 100 | 8 |
| B-8 | 87.5 | 8 | 100 | 8 |
| B-9 | 87.5 | 8 | 100 | 8 |
| B-10 | 75.0 | 8 | 100 | 8 |
| | Average = 81.3 | | Average = 100 | |

*Sample number: B-# where # is a multiple of about 6000 cigarettes; for example, B-10 refers to about 100 articles taken after about 60,000 cigarettes were made.
**NIST (10-sheet) filter paper IP test

TABLE 4

IP and Freeburn Results for Samples of 1-C Acquired During A Manufacturing Trial.

| Grab Samples | IP Pass (%)* | Replicates | Freeburn (%) | Replicates |
|---|---|---|---|---|
| C-1 | 100 | 8 | 100 | 8 |
| C-2 | 87.5 | 8 | 87.5 | 8 |
| C-3 | 100 | 8 | 87.5 | 8 |
| C-4 | 75.0 | 8 | 100 | 8 |
| C-5 | 87.5 | 8 | 100 | 8 |
| C-6 | 87.5 | 8 | 100 | 8 |
| C-7 | 100 | 8 | 100 | 8 |
| C-8 | 100 | 8 | 100 | 8 |
| C-9 | 100 | 8 | 100 | 8 |
| C-10 | 100 | 8 | 87.5 | 8 |
| | Average = 93.8 | | Average = 91.3 | |

*Sample number: C-# where # is a multiple of about 6000 cigarettes; for example, C-10 refers to about 100 articles taken after about 60,000 cigarettes were made.
**NIST (10-sheet) filter paper IP test

EXAMPLE 2

A survey of derivatized starch products was made to determine their suitability for use in preparing a cigarette having reduced IP. RediFilm-54®, RediFilm-250®, and 11527–2 starch compositions were obtained from National Starch (Berkeley, Calif.) as summarized Table 5.

The various starch compositions were used to make a circumferential band, about 7 millimeters wide, around the body of a smoking article. The circumferential band was positioned about 15 millimeters from the ignition end of the finished smoking article. The smoking article was prepared using cigarette paper A, an about 63 millimeter tobacco column length, an about 21 millimeter cellulose acetate non-air diluted filter section, and a cigarette tobacco blend.

TABLE 5

Starch Compositions Used.

| Starch Product* | Characterization |
|---|---|
| RediFilm-54 ® | hydrophobic derivatized starch "low" degree of substitution water-based composition at 24.66 weight percent solids |
| RediFilm-250 ® | hydrophobic derivatized starch "high" degree of substitution water-based composition at 23.67 weight percent solids |
| 11527-2 | hydrophobic derivatized starch experimental, non-commercial product water-based composition at 9.33 weight percent solids |

*Supplied by National Starch (Berkeley, CA)

A band was applied on the smoking article by hand using an aluminum printing plate, and the wet weight of added material was measured. The applied dry weights of banding materials were calculated and are reported in Table 6.

The NIST (#6) cotton duck IP test was used to determine IP of the banded cigarette samples. For each banded cigarette type, 8 replicates were tested and the results are given in Table 6:

TABLE 6

Summary of Banded Cigarette IP Data.

| Starch Product | IP Pass (%)* | Dry band weight ($\mu$g) |
|---|---|---|
| RediFilm-54 ® | 100 | 222 |
| | 100 | 113 |
| | 100 | 88 |
| | 62.5 | 44 |
| RediFilm-250 ® | 100 | 156 |
| | 100 | 88 |
| | 12.5 | 38 |
| 11527-2 | 100 | 94 |
| | 12.5 | 36 |

*NIST (#6) cotton duck IP test

The hydrophobic derivatized starches (RediFilm-54®, RediFilm-250®, and 11527-2) gave low visibility bands when applied on the cigarettes. The IP results indicate that derivatized starch products are effective IP reducing materials. In the present application about 90 micrograms ($\mu$g) would be the dry weight that forms a substantially about 100% effective, IP reducing, registered position band.

EXAMPLE 3

Three smoking articles were made using a banded wrapper, an about 63 millimeter tobacco column length, an about 21 millimeter cellulose acetate non-air diluted filter section, and cigarette tobacco blend. The cigarettes were made on a conventional cigarette-making machine. The smoking articles were made using separate banded cigarette papers.

Cigarette type 3-A was made from cigarette paper A gravure printed with a composition containing about 16.4 weight percent RediFilm-54® starch (National Starch, Berkeley, Calif.) and about 83.6 weight percent tap water. The permeability in the banded region was measured as about 4 CU.

Cigarette type 3-B was made from cigarette paper A gravure printed with a composition containing about 18.18 weight percent Ethylex-2015® hydroxyethylated starch (A. E. Staley, Decatur, Ill.), about 1.01 weight percent DAP (Rhodia, Cranbury, N.J.), and about 80.81 weight percent tap water. The composition heated at approximately 87° C. for about 15 minutes.

Cigarette type 3-C was made from cigarette paper A gravure printed with a composition containing about 18.18 weight percent Ethylex-2065® hydroxyethylated starch (A. E. Staley, Decatur, Ill.), about 1.01 weight percent DAP (Rhodia, Cranbury, N.J.), and about 80.81 weight percent tap water. The composition was heated at approximately 87° C. for about 15 minutes.

During cigarette production, approximately 2,000 cigarettes were collected for each type. The cigarettes were collected such that the individual cigarettes were randomly mixed in a collection box. Therefore, the band positions on the manufactured cigarettes may be characterized as random. The derivatized starches (RediFilm-54®, Ethylex-2015®, and Ethylex-2065®) gave low visibility bands when applied on the cigarettes.

The banded, reduced IP, papers ran substantially the same as non-banded cigarette paper A. No manufacturing problems were observed during cigarette production.

Table 7 indicates IP and freeburn results for cigarettes 3-A, 3-B, and 3-C. Cigarette IP was measured, using about 20 replicates, by the NIST (10-sheet) filter paper test. The freeburn character was measured using about 16 replicates. The IP results indicate that derivatized starch products are effective IP reducing materials in the present application in which band position is random on the individual articles in the population.

TABLE 7

Summary of Banded Cigarette IP and Freeburn Data.

| Cigarette Type | Starch Product | IP Pass (%)* | Freeburn (%) |
|---|---|---|---|
| 3-A | RediFilm-54 ® | 100 | 0.0 |
| 3-B | Ethylex-2015 ® | 90 | 93.8 |
| 3-C | Ethylex-2065 ® | 100 | 0.0 |

*NIST (10-sheet) filter paper IP test

EXAMPLE 4

A series of cigarette types banded with compositions containing varying Flokote-64® starch (National Starch, Berkeley, Calif.) contents was prepared. Compositions were prepared by combining an appropriate amount of starch powder in tap water as summarized in Table 8. The starch/water combination was heated at approximately 90° C. for about 10 minutes.

Cigarette types 4-A, 4-B, 4-C, 4-D, and 4-E were made from cigarette papers gravure printed with starch compositions as listed in Table 8 and 9. Gravure printing was performed using an about 8 millimeter band width and an about 25 millimeter center-to-center spacing. Smoking articles were made using separate banded wrappers, an about 63 millimeter tobacco column length, an about 21 millimeter cellulose acetate non-air diluted filter section, and a cigarette tobacco blend. The cigarettes were made on a conventional cigarette-making machine.

During cigarette production, approximately 2,000 cigarettes were collected. The cigarettes were collected such that the individual cigarettes were randomly mixed in a collection box. Therefore, the band positions on the manufactured cigarettes may be characterized as random. The starch compositions gave low visibility bands when applied on the cigarettes.

TABLE 8

Starch Compositions Used.

| Composition # | Starch (g) | Water (mL) | Composition (%)* |
|---|---|---|---|
| 4-1 | 600 | 4000 | 13.04 |
| 4-2 | 750 | 4000 | 15.79 |
| 4-3 | 850 | 4000 | 17.53 |
| 4-4 | 1000 | 4000 | 20.00 |

*Weight percent composition Flokote-64 ® starch (National Starch, Berkeley, CA)

TABLE 9

Permeability of Banded Cigarette Paper.

| Cigarette Type | Base Paper | Band Solution* | Band Perm. (CU)** |
|---|---|---|---|
| 4-A | A | 4-1 | 10 |
| 4-B | A | 4-2 | 8 |
| 4-C | A | 4-3 | 6 |
| 4-D | A | 4-4 | 4 |
| 4-E | B | 4-4 | 5 |

*See Table 7
**Perm. = permeability

Table 10 indicates IP and freeburn results for cigarette types 4-A, 4-B, 4-C, 4-D, and 4-E. Cigarette IP was measured, using about 20 replicates, by the NIST (10-sheet) filter paper test. The freeburn character was measured using about 6 replicates. The results indicate that significant IP reduction occurs when the band permeability is reduced to less than about 6 CU. The applied permeability reducing agent may be adjusted, such as controlling percent weight, viscosity or the like, to give an effective IP reducing band in the present application in which band position is random on the individual articles in the population.

TABLE 10

Summary of Banded Cigarette IP and Freeburn Data.

| Cigarette Type | IP Pass (%)* | Freeburn (%) |
|---|---|---|
| 4-A | 0 | 100 |
| 4-B | 0 | 100 |
| 4-C | 40 | 100 |
| 4-D | 95 | 95 |
| 4-E | 85 | 100 |

*NIST (10-sheet) filter paper IP test

Applicants evaluated the smoke taste profile of cigarette type 4-D. The taste when smoking within banded areas differed from the taste in the untreated, non-banded, areas. The band region was characterized as possessing less taste strength and a slight paper-like taste relative to the untreated, non-banded, region.

EXAMPLE 5

A series of cigarette types banded with compositions containing varying Flokote-64® starch (National Starch, Berkeley, Calif.) and DAP (Rhodia, Cranbury, N.J.) contents was prepared. Compositions were prepared by combining an appropriate amount of starch powder and DAP in tap water as summarized in Table 11. The combinations were heated at approximately 90° C. for about 15 minutes.

Cigarette types 5-A through 5-L were made from cigarette papers gravure printed with starch compositions as listed in Table 11 and 12. All cigarette types had a band configuration of about 6 millimeter width and about 25 millimeter center-to-center spacing except types 5-I and 5-J which had a band configuration of about 8 millimeter width and about 25 millimeter center-to-center spacing.

Smoking articles were made using separate banded wrappers, an about 63 millimeter tobacco column length, an about 21 millimeter cellulose acetate non-air diluted filter section, and a cigarette tobacco blend. The cigarettes were made on a conventional cigarette-making machine.

TABLE 11

Starch Compositions Used.

| Composition # | Starch (g) | DAP (g) | Water (mL) | Composition* |
|---|---|---|---|---|
| 5-1 | 900 | 0 | 4000 | 18.37% S |
| 5-2 | 900 | 12.5 | 4000 | 18.27% S, 0.25% DAP |
| 5-3 | 900 | 25 | 4000 | 18.32% S, 0.51% DAP |
| 5-4 | 900 | 50 | 4000 | 18.18% S, 1.01% DAP |
| 5-5 | 900 | 150 | 4000 | 17.82% S, 2.97% DAP |
| 5-6 | 900 | 200 | 4000 | 17.65% S, 3.92% DAP |
| 5-7 | 900 | 300 | 4000 | 17.31% S, 5.77% DAP |
| 5-8 | 1000 | 0 | 4000 | 20.00% S |
| 5-9 | 1040 | 150 | 4000 | 20.04% S, 2.89% DAP |
| 5-10 | 1100 | 50 | 4000 | 21.36% S, 0.97% DAP |
| 5-11 | 1250 | 50 | 4000 | 23.58% S, 0.94% DAP |

*Weight percent composition:
S = Flokote-64 ® starch (National Starch, Berkeley, CA),
DAP = diammonium phosphate (Rhodia, Cranbury, NJ)

During cigarette manufacture, approximately 2,000 cigarettes were collected. The cigarettes were collected such that the individual cigarettes were randomly mixed in a collection box. Therefore, the band positions on the manufactured cigarettes may be characterized as random. The starch compositions gave low visibility bands when applied on the cigarettes.

Table 13 indicates IP and freeburn results for cigarette types 5-A through 5-L. Cigarette IP was measured, using about 20 replicates, by the NIST (10-sheet) filter paper test. The freeburn character was measured using about 16 replicates. The results indicate that significant IP reduction occurs when the band permeability is less than about 6 CU, although for the present example freeburn was significantly lowered for the about 4 CU and about 3 CU band permeability samples.

TABLE 12

Permeability of Banded Cigarette Paper.

| Cigarette Type | Base Paper | Band Solution* | Band Perm. (CU)** |
|---|---|---|---|
| 5-A | A | 5-1 | 6 |
| 5-B | A | 5-2 | -- |
| 5-C | A | 5-3 | -- |
| 5-D | A | 5-4 | 6 |
| 5-E | A | 5-5 | 6 |
| 5-F | A | 5-6 | 6 |
| 5-G | A | 5-7 | 6 |

TABLE 12-continued

Permeability of Banded Cigarette Paper.

| Cigarette Type | Base Paper | Band Solution* | Band Perm. (CU)** |
|---|---|---|---|
| 5-H | A | 5-8 | -- |
| 5-I | A | 5-9 | 3 |
| 5-J | B | 5-9 | 4 |
| 5-K | A | 5-10 | -- |
| 5-L | A | 5-11 | -- |

*See Table 11
**Perm. = permeability
--= not determined

TABLE 13

Summary of Banded Cigarette IP and Freeburn Data.

| Cigarette Type | IP Pass (%)* | Freeburn (%) |
|---|---|---|
| 5-A | 90 | 100 |
| 5-B | 100 | 93.8 |
| 5-C | 100 | 93.8 |
| 5-D | 100 | 100 |
| 5-E | 100 | 93.8 |
| 5-F | 100 | 100 |
| 5-G | 90 | 93.8 |
| 5-H | 100 | 0 |
| 5-I | 100 | 0 |
| 5-J | 100 | 10 |
| 5-K | 100 | 0 |
| 5-L | 100 | 6.3 |

*NIST (10-sheet) filter paper IP test

Applicants evaluated the smoke taste profile of cigarette types 5-A through 5-G. The taste when smoking within banded areas differed from the taste in the untreated, non-banded, areas. The band region was characterized as possessing less taste strength relative to the untreated, non-banded, region. In contrast to cigarette type 4-D (Example 4), the presence of DAP eliminated the slight paper-like taste attributed to using a permeability reducing agent alone to form the banded region. Moreover, composition 5–4 (1.01 weight percent DAP) was sufficient to afford the maximal benefit of DAP presence. Higher contents of DAP, such as composition 5–7, tended to increase the width of the char line as the banded region was smoked through.

EXAMPLE 6

A series of cigarette types banded with compositions containing varying Flokote-64® starch (National Starch, Berkeley, Calif.) and DAP (Rhodia, Cranbury, N.J.), and sodium/potassium citrate salt contents was prepared. Smoking articles were made using separate banded wrappers, an about 63 millimeter tobacco column length, an about 21 millimeter cellulose acetate non-air diluted filter section, and a cigarette tobacco blend. The cigarettes were made on a conventional cigarette-making machine.

Cigarette type 6-A was made from cigarette paper A gravure printed with a composition containing about 20.65 weight percent Flokote-64® starch (National Starch, Berkeley, Calif.), about 0.94 weight percent DAP (Rhodia, Cranbury, N.J.), 3.32 weight percent citrate salt, and about 75.09 weight percent tap water. The citrate salt was a mixture of sodium citrate dihydrate (Fisher Scientific, Fair Lawn, N.J.) and potassium citrate monohydrate (Fisher Scientific, Fair Lawn, N.J.) in an about 1:2.8 weight/weight ratio. The composition was heated at approximately 87° C. for about 15 minutes.

Cigarette type 6-B was made from cigarette paper A gravure printed with a composition containing about 21.36 weight percent Flokote-64® starch (National Starch, Berkeley, Calif.), about 0.97 weight percent DAP (Rhodia, Cranbury, N.J.), and about 77.67 weight percent tap water. The composition was heated approximately 87° C. for about 15 minutes.

Cigarette type 6-C was made from cigarette paper A gravure printed with a composition containing about 19.56 weight percent Flokote-64® starch (National Starch, Berkeley, Calif.), about 0.89 weight percent DAP (Rhodia, Cranbury, N.J.), about 8.44 weight percent citrate salt, and about 71.11 weight percent tap water. The citrate salt was a mixture of sodium citrate dihydrate (Fisher Scientific, Fair Lawn, N.J.) and potassium citrate monohydrate (J. T. Baker, Phillipsburg, N.J.) in an about 1:2.8 weight/weight ratio. The composition was heated at approximately 87° C. for about 15 minutes.

During cigarette manufacture, approximately 2,000 cigarettes were collected. The cigarettes were collected such that the individual cigarettes were randomly mixed in a collection box. Therefore, the band positions on the manufactured cigarettes may be characterized as random. The starch compositions gave low visibility bands when applied on the cigarettes.

Table 14 indicates IP and freeburn results for cigarette types 6-A, 6-B, and 6-C. Cigarette IP was measured, using about 20 replicates, by the NIST (10-sheet) filter paper test. The freeburn character was measured using about 64 replicates for article types 6-A and 6-B and about 16 replicates for article type 6-C.

TABLE 14

Summary of Banded Cigarette IP and Freeburn Data.

| Cigarette Type | IP Pass (%)* | Freeburn (%) |
|---|---|---|
| 6-A | 100 | 87.5 |
| 6-B | 100 | 34.4 |
| 6-C | 100 | 90.0 |

*NIST (10-sheet) filter paper IP test

Both the burn rate retarding substance (such as DAP) and the burn rate accelerating substance (such as sodium/potassium citrate salt) are beneficial band additives that influence the ability of the article to freeburn. High levels of the permeability reducing substance (such as starch) deposited in the band may increase the IP pass rate of the cigarette (see Example 4), but will decrease the ability of the cigarette to freeburn particularly when combined with the burn rate retarding substance (see Example 5). The burn rate accelerating substance (such as sodium/potassium citrate salt) is a beneficial band component because this burn promoter can be used to increase the ability of a heavily banded cigarette to freeburn while maintaining concurrent reduced IP character.

Furthermore, applicants have discovered the unexpected organoleptic enhancing abilities of the burn rate accelerating substance preferably in combination with the burn rate retarding substance. The smoke taste profile of cigarette 6-C was substantially consistent when smoking within banded areas and smoking in the untreated, non-banded, areas.

EXAMPLE 7

Two smoking articles were made using a banded wrapper, an about 63 millimeter tobacco column length, an about 21 millimeter cellulose acetate non-air diluted filter section, and cigarette tobacco blend. The cigarettes were made on a conventional cigarette-making machine. The smoking articles were made using separate banded cigarette papers.

Cigarette type 7-A was made from cigarette paper A gravure printed with a composition containing about 18.18 weight percent Flokote-64® starch (National Starch, Berkeley, Calif.), about 1.01 weight percent monoammonium phosphate (Fisher Scientific, Fair Lawn, N.J.), and about 80.81 weight percent tap water. The composition was heated at approximately 87° for about 15 minutes.

Cigarette type 7-B was made from cigarette paper A gravure printed with a composition containing about 17.82 weight percent Flokote-64® starch (National Starch, Berkeley, Calif.), about 2.97 weight percent monoammonium phosphate (Fisher Scientific, Fair Lawn, N.J.), and about 79.21 weight percent tap water. The composition was heated at approximately 87° C. for about 15 minutes.

During cigarette production, approximately 2,000 cigarettes were collected for each type. The cigarettes were collected such that the individual cigarettes were randomly mixed in a collection box. Therefore, the band positions on the manufactured cigarettes may be characterized as random. The banded, reduced IP, papers ran substantially the same as non-banded cigarette paper A. No manufacturing problems were observed during cigarette production.

Table 15 indicates IP and freeburn results for cigarettes 7-A and 7-B. Article IP was measured, using about 20 replicates, by the NIST (10-sheet) filter paper test. The freeburn character was measured using about 16 replicates. The IP results indicate that starch combined with monoammonium phosphate is an effective IP reducing material in the present application in which band position is random on the individual articles in the population.

TABLE 15

Summary of Banded Cigarette IP and Freeburn Data.

| Cigarette Type | IP Pass (%)** | Freeburn (%) |
|---|---|---|
| 7-A | 100 | 43.8 |
| 7-B | 100 | 62.5 |

**NIST (10-sheet) filter paper IP test

EXAMPLE 8

One smoking articles was made using a banded wrapper, an about 63 millimeter tobacco column length, an about 21 millimeter cellulose acetate non-air diluted filter section, and cigarette tobacco blend. The cigarette was made on a conventional cigarette-making machine.

Cigarette type 8-A was made from cigarette paper A gravure printed with a composition containing about 15.24 weight percent Flokote-64® starch (National Starch, Berkeley, Calif.), about 0.95 weight percent DAP (Rhodia, Carnbury, N.J.), about 7.62 weight percent microcrystalline cellulose (Aldrich, Milwaukee, Wis., Catalog #31,069-7), and about 76.19 weight percent tap water. The starch/DAP composition heated at approximately 87° C. for about 15 minutes then the cellulose component was dispersed before printing.

During manufacturing, approximately 2,000 articles of type 8-A were collected. The cigarettes were collected such that the individual cigarettes were randomly mixed in a collection box. Therefore, the band positions on the manufactured cigarettes may be characterized as random. The banded, reduced IP, papers ran substantially the same as non-banded cigarette paper A. No manufacturing problems were observed during cigarette production.

The composition used to band article type 8-B contained about 14.61 weight percent Flokote-64® starch (National Starch, Berkeley, Calif.), about 0.97 weight percent DAP (Rhodia, Carnbury, N.J.), about 2.16 weight percent sodium citrate dihydrate (Fisher Scientific, Fair Lawn, N.J.), about 6.05 weight percent potassium citrate monohydrate (J. T. Baker, Phillipsburg, N.J.), about 4.40 weight percent colloidal cellulose (Aldrich, Milwaukee, Wis.; Catalog #43,524-4), and about 71.82 weight percent tap water. The starch/DAP/citrate salt composition was heated at approximately 90° C. for about 20 minutes then the cellulose component was dispersed before applying the material to articles.

Cigarette type 8-B was hand banded with the starch/DAP/cellulose composition to give a circumferential band, about 7 millimeters wide, around the body of a smoking article. The circumferential band was positioned about 20 millimeters from the ignition end of the finished article. The smoking article was prepared using cigarette paper A, an about 72 millimeter tobacco column length, an about 25 millimeter cellulose acetate non-air diluted filter section, and a cigarette tobacco blend.

The fixed-position band of article type 8-B was applied on the smoking article by hand using an aluminum printing plate, and the wet weight of added material was measured. The applied total dry weight of banding material was calculated to be about 1.4 milligrams.

Table 16 indicates IP and freeburn results for cigarettes 8-A and 8-B. Cigarette IP was measured, using about 20 replicates for 8-A and 4 replicates for 8-B, by the NIST (10-sheet) filter paper test. The freeburn character was measured using about 16 replicates for 8-A and 4 replicates for 8-B. The IP results indicate that starch/DAP, or more preferably starch/DAP/citrate salt, combined with cellulose is an effective IP reducing material in the present application in which band position is either random or fixed on the individual articles in the population.

TABLE 16

Summary of Banded Cigarette IP and Freeburn Data.

| Cigarette Type | IP Pass (%)* | Freeburn (%) |
|---|---|---|
| 8-A | 45 | 100 |
| 8-B | 100 | 100 |

*NIST (10-sheet) filter paper IP test

EXAMPLE 9

Cigarette types 9-A and 9-B were hand banded with compositions to give a circumferential band, about 7 millimeters wide, around the body of a smoking article. The circumferential band was positioned about 20 millimeters from the ignition end of the finished article. The smoking article was prepared using cigarette paper A, an about 72 millimeter tobacco column length, an about 25 millimeter cellulose acetate non-air diluted filter section, and a cigarette tobacco blend.

The fixed-position band of was applied on the smoking article by hand using an aluminum printing plate, and the wet weight of added material was measured. The applied dry weights of banding materials were calculated and found to be about 1.4 milligrams (total dry material weight) for article type 9-A and about 0.82 milligrams (total dry material weight) for article type 9-B.

The composition used to band article type 9-A contained about 14.47 weight percent Flokote-64® starch (National Starch, Berkeley, Calif.), 0.96 weight percent DAP (Rhodia, Carnbury, N.J.), about 2.14 weight percent sodium citrate dihydrate (Fisher Scientific, Fair Lawn, N.J.), about 6.00 weight percent potassium citrate monohydrate (J. T. Baker, Phillipsburg, N.J.), about 5.30 weight percent calcium carbonate (Aldrich, Milwaukee, Wis.; Catalog #31,003-4), and about 71.14 weight percent tap water. The starch/DAP/citrate salt composition was heated at approximately 90° C. for about 20 minutes then the calcium carbonate component was dispersed before applying the material to the articles.

The composition used to band article type 9-B contained about 14.56 weight percent Flokote-64® starch (National Starch, Berkeley, Calif.), 0.96 weight percent DAP (Rhodia, Carnbury, N.J.), about 2.15 weight percent sodium citrate dihydrate (Fisher Scientific, Fair Lawn, N.J.), about 6.04 weight percent potassium citrate monohydrate (J. T. Baker, Phillipsburg, N.J.), about 4.70 weight percent Kaolin clay (Aldrich, Milwaukee, Wis.; Catalog #22,883-4), and about 71.59 weight percent tap water. The starch/DAP/citrate salt composition was heated at approximately 90° C. for about 20 minutes then the Kaolin clay component was dispersed before applying the material to the articles.

Table 17 indicates IP and freeburn results for cigarettes 9-A and 9-B. Cigarette IP was measured, using about 4 replicates, by the NIST (10-sheet) filter paper test. The freeburn character was measured using about 4 replicates. The IP results indicate that starch/DAP/citrate salt combined with filler, such as calcium carbonate, clay, and the like, is an effective IP reducing material in the present application in which band position is fixed on the individual articles in the population.

Applicants anticipate that the composition applied to articles may be adjusted due to synergistic interactions between filler and other band components. For example, article 9-B incorporates Kaolin clay as a band component, which appears to synergistically enhance the performance of the bum rate retarding substance and/or the permeability reducing substance. As a further example, article 9-A incorporates an alkaline-earth metal containing salt, calcium carbonate, known to act as paper burn rate accelerating substance, which may interact synergistically with the burn rate accelerating component. Alternatively, the filler component may cooperate with the permeability reducing substance.

TABLE 17

Summary of Banded Cigarette IP and Freeburn Data.

| Cigarette Type | IP Pass (%)* | Freeburn (%) |
|---|---|---|
| 9-A | 100 | 100 |
| 9-B | 100 | 25 |

*NIST (10-sheet) filter paper IP test

EXAMPLE 10

A series of base cigarette papers were banded with a composition containing Flokote-64® starch (National Starch, Berkeley, Calif.) and DAP (Rhodia, Cranbury, N.J.). Smoking articles were made using separate banded wrappers, an about 63 millimeter tobacco column length, an about 21 millimeter cellulose acetate non-air diluted filter section, and a cigarette tobacco blend. The cigarettes were made on a conventional cigarette-making machine.

Cigarette types were made from a series of cigarette papers, as listed in Table 18, gravure printed with a composition containing about 21.36 weight percent Flokote-64® starch (National Starch, Berkeley, Calif.), about 0.97 weight percent DAP (Rhodia, Cranbury, N.J.), and about 77.67 weight percent tap water. The composition was heated at approximately 87° C. for about 15 minutes.

TABLE 18

Summary of Banded Cigarette IP and Freeburn Data.

| Cigarette Type | Base Paper | IP Pass (%)* | Freeburn (%) |
|---|---|---|---|
| 10-A | A | 100 | 34 |
| 10-B | D | 100 | 56.3 |
| 10-C | E | 100 | 57.0 |
| 10-D | F | 100 | 62.5 |
| 10-E | G | 80 | 100 |
| 10-F | A** | 100 | 43.8 |
| 10-G | H | 50 | 100 |

*NIST (10-sheet) filter paper IP test
**Base paper A electrostatically perforated to about 70 CU During manufacturing, approximately 2,000 articles of type 10-A through 10-G were collected. The cigarettes were collected such that the individual cigarettes were randomly mixed in a collection box. Therefore, the band positions on the manufactured cigarettes may be characterized as random. The banded, reduced IP, papers ran substantially the same as non-banded cigarette paper A. No manufacturing problems were observed during cigarette production.

The IP and freeburn data in Table 18 demonstrate that at constant applied band composition, and application method, results may vary depending on the structure of the base paper. Articles prepared from the higher permeability papers, 10-E and 10-H, showed lower IP pass rates than articles 10-A through 10-F. Applicants believe that increasing the applied amount of the composition will increase IP pass rate for higher base paper permeability types (such as 10-E and 10-G). For articles 10-A through 10-D and 10-F applicants fully expect that the freeburn value may be increased by the incorporation of a burn rate accelerating substance in the band.

Article type 10-F used an about 18 CU base paper (A) electrostatically perforated, before band printing, to about 70 CU. After banding, the permeability in the band region was measured as about 57 CU. Article type 10-A, utilizing base paper A, had a measured band permeability of about 5 CU. Interestingly, article types 10-A and 10-F gave similar IP and freeburn results. This example demonstrates the unexpected result that perforation in the banded region, at the level applied, does not degrade the IP performance. Applicants fully anticipate higher levels of perforation may give similar results.

An important consideration for the design of commercially acceptable reduced IP articles is product smoke delivery. Smoke delivery is the quantity of various smoke components produced by the article during its consumption. For this example, carbon monoxide was used as a surrogate for all components delivered by the article. An article manufactured from a paper containing a banded region of lower permeability than the non-banded region may display increased smoke delivery relative to the non-banded control article. The width, spacing, composition, and number of the bands may also affect smoke delivery changes.

For example in Table 19, an article type prepared from base paper A gave a carbon monoxide delivery of about 18.2 milligrams/cigarette, but the same wrapper in a banded state (band permeability about 5 CU) caused the delivery to increase to about 21.3 milligrams/cigarette. Applicants have demonstrated that substituting a higher permeability base paper will afford smoke deliveries similar to the control type (for example 10-B through 10-G versus control).

Additionally, applicants have discovered the unexpected result that incorporating a burn accelerating substance in the band (such as article type 6-C) can give a lower smoke delivery relative to the banded article not containing the burn accelerating substance (such article type 10-A).

TABLE 19

Carbon Monoxide Content of Banded and Control Articles.

| Cigarette Type | Carbon Monoxide (milligrams/cigarette) |
|---|---|
| Control* | 18.2 |
| 10-A | 21.3 |
| 6-C | 20.6 |
| 10-B | 18.3 |
| 10-C | 18.4 |
| 10-D | 17.6 |
| 10-E | 17.3 |
| 10-F | 18.5 |
| 10-G | 17.6 |

*Control, non-banded, article manufactured with base paper A

Certain modifications and improvements will occur to those skilled in the art upon a reading of the foregoing description. By way of example, an alternative method for controlling smoke delivery may be used. Examples of such alternative methods include diluting filter smoke with air, changing tobacco blend, and altering base paper burn regulator composition. It should be understood that all such modifications and improvements have been deleted herein for the sake of conciseness and readability but are properly within the scope of the following claims.

We claim:

1. A smoking article having reduced ignition propensity comprising:
    a tobacco column and
    a wrapper surrounding the tobacco column and having a base permeability, the wrapper comprising:
        an untreated area and
        a least one discrete area treated with a
            a permeability reducing substance;
            a burn rate retarding substance; and
            a burn rate accelerating substance,
        wherein the at least one discrete area has a lower permeability than the base permeability of the wrapper.

2. The smoking article of claim 1 further comprising a filter element.

3. A wrapper for a smoking article having reduced ignition propensity, the wrapper having a base permeability and comprising:
    at least one untreated area and
    at least one discrete area treated with a
        a permeability reducing substance,
        a burn rate retarding substance and
        a burn rate accelerating substance,
    wherein the at least one discrete area has a lower permeability than the base permeability of the wrapper.

4. The wrapper according to claim 3 wherein at least one of said burn rate retarding substance and said burn rate accelerating substance is further an organoleptic enhancing substance that substantially reduces any difference in a smoker's experience between the smoking of said at least one discrete treated area and said at least one untreated area during smoking of the smoking article.

5. The wrapper according to claim 3 wherein a consistency of the combination of the permeability reducing substance, the burn rate retarding substance and the burn rate accelerating substance is such as to be applicable to the wrapper.

6. The wrapper according to claim 5 wherein a consistency of the combination of the permeability reducing substance, the burn rate retarding substance and the burn rate accelerating substance is such as to be applicable to the wet wrapper.

7. The wrapper according to claim 5 wherein a consistency of the combination of the permeability reducing substance, the burn rate retarding substance and the burn rate accelerating substance is such as to be applicable to the dry wrapper.

8. The wrapper according to claim 3 wherein said burn rate accelerating substance is salt.

9. The wrapper according to claim 8 wherein said salt is one of an alkali metal containing compound and an alkaline-earth metal containing compound.

10. The wrapper according to claim 9 wherein said one of an alkali metal containing compound and an alkaline-earth metal containing compound is a salt of a carboxylic acid.

11. The wrapper according to claim 10 wherein said salt of a carboxylic acid is a salt of at least one of acetic acid, citric acid, malic acid, lactic acid, glycolic acid, tartaric acid, fumaric acid, maleic acid, malonic acid, glutaric acid, adipic acid and succinic acid.

12. The wrapper according to claim 10 wherein said salt of a carboxylic acid is a salt of citric acid.

13. The wrapper according to claim 9 wherein said alkali metal containing compound is a sodium containing compound.

14. The wrapper according to claim 9 wherein said alkali metal containing compound is a potassium containing compound.

15. The wrapper according to claim 3 wherein the burn rate retarding substance is a phosphate.

16. The wrapper according to claim 15 wherein said phosphate is a phosphate of ammonium.

17. The wrapper according to claim 16 wherein said phosphate of ammonium is diammonium phosphate.

18. The wrapper according to claim 3 wherein said permeability reducing substance is a pore filling substance thereby reducing permeability of the at least one discrete treated area.

19. The wrapper according to claim 3 wherein said permeability reducing substance is a film forming substance thereby reducing permeability of said at least one discrete treated area.

20. The wrapper according to claim 3 wherein said permeability reducing substance is a polymer.

21. The wrapper according to claim 20 wherein said polymer is a polysaccharide.

22. The wrapper according to claim 21 wherein the polysaccharide is water soluble.

23. The wrapper according to claim 21 wherein the polysaccharide is water dispersible.

24. The wrapper according to claim 21 wherein said polysaccharide is at least one of starch, modified starch and a starch derivative.

25. The wrapper according to claim 24 wherein the polysaccharide is water soluble.

26. The wrapper according to claim 24 wherein the polysaccharide is water dispersible.

27. The wrapper according to claim 21 wherein the polysaccharide is at least one of cellulose and a cellulose derivative.

28. The wrapper according to claim 21 wherein to the polysaccharide is at least one of chitosan and a chitosan derivative.

29. The wrapper according to claim 21 wherein the polysaccharide is at least one of chitin and a chitin derivative.

30. The wrapper according to claim 21 wherein the polysaccharide is at least one of alginate and an alginate derivative.

31. The wrapper according to claim 3 wherein the discretely treated area comprises a circumferential band.

32. The wrapper according to claim 31 wherein the circumferential band has a sufficient width so as to deprive the coal of the burning tobacco firecone of oxygen from behind a char line of the wrapper.

33. The wrapper according to claim 31 wherein the circumferential band has a width of at least about 3 millimeters.

34. The wrapper according to claim 3 wherein the at least one discrete treated area comprises at least two bands spaced sufficiently to reduce the ignition propensity of the smoking article.

35. The wrapper according to claim 34 wherein the at least two circumferential bands have widths and are spaced apart so that a width/center-to-center spacing ratio is between about 1/10 and about 1/1.

36. The wrapper according to claim 34 wherein the at least two circumferential bands have widths between about 3 millimeters and about 10 millimeters.

37. The wrapper according to claim 34 wherein the at least two circumferential bands have a center-to-center spacing of about 10 millimeters to about 30 millimeters.

38. The wrapper according to claim 3 that has properties that enable a bobbin of wrapper to be useable in a conventional commercially available cigarette manufacturing machine.

39. The wrapper according to claim 3 wherein the at least one discrete area is visually substantially the same as the untreated area.

40. A method for making a smoking article having reduced ignition propensity comprising:
   forming a paper having a base permeability;
   treating a plurality of discrete areas of the paper with a permeability reducing substance, a burn rate retarding substance and a burn accelerating substance;
   forming the paper into a wrapper for a smoking article; and
   surrounding a tobacco column having a proximal end and a distal end with at least a portion of the wrapper so that at least one discretely treated area substantially surrounds the tobacco column between the ends or the wrapper-surrounded tobacco column so that as a coal of burning tobacco firecone advances by said at least one discrete treated area, the smoking article self-extinguishes if placed on a surface.

41. A method for making a wrapper for a smoking article having reduced ignition propensity comprising:
   forming a paper having a base permeability;
   treating a plurality of discrete areas of the paper with a permeability reducing substance, a burn rate retarding substance and a burn rate accelerating substance, wherein at least one of said burn rate retarding substance and said burn rate accelerating substance is further an organoleptic enhancing substance that substantially reduces any difference in a smoker's experience between the smoking of said differently treated areas and untreated areas; and forming the paper into a wrapper for a smoking article.

42. A method for making a smoking article having reduced ignition propensity comprising:
   forming a paper having a base permeability;
   treating a plurality of discrete areas of the paper with a permeability reducing substance, a burn rate reducing substance and a burn rate accelerating substance;
   forming the paper into a wrapper for a smoking article;
   surrounding a tobacco column having a proximal end and a distal end with at least a portion of the wrapper so that at least one discrete treated area is between the ends of the wrapper-surrounded tobacco column so that as a coal of a burning tobacco firecone advances by said at least one discrete treated area, the smoking article self-extinguishes if placed on a surface; and
   adding a filter element to at least one end of the wrapper-surrounded tobacco column, wherein at least one of said burn rate retarding substance and said burn rate accelerating substance is further an organoleptic enhancing substance that substantially reduced any difference in a smoker's experience between the smoking of said at least one treated area and said untreated area during smoking of the smoking article.

43. A smoking article comprising:
   a tobacco column,
   a wrapper surrounding the tobacco column and having at least one circumferential band comprising starch, diammonium phosphate and a burn rate accelerating substance comprising a salt of citric acid.

44. The smoking article according to claim 43 wherein the at least one circumferential band is made of an applied ink of about 14 to about 27% starch, up to about 11% burn rate accelerating substance comprising at least one alkali metal citrate salt and up to about 5% diammonium phosphate.

45. The smoking article according to claim 43 wherein the band is made of an ink of about 18 to about 24% starch, about 2 to about 9% burn rate accelerating substance comprising at least one alkali metal citrate salt, and about 1% diammonium phosphate.

46. The smoking article according to claim 43 wherein the wrapper has at least one untreated area having a permeability of between about 18 CORESTA units and about 71 CORESTA units.

47. The smoking article according to claim 43, wherein the band is made of an ink of about 20 to about 22% starch, about 5 to about 9% burn rate accelerating substance comprising at least one alkali metal citrate salt, and about 1% diammonium phosphate.

48. The smoking article according to claim 43, wherein the bend is made of an ink of about 14 to about 27% starch, up to about 11% burn rate accelerating substance comprising at least one alkali metal citrate salt selected from the group consisting of sodium citrate and potassium citrate, said up to about 5% diammonium phosphate.

49. A smoking article having reduced ignition propensity comprising:
   (a) a tobacco column;
   (b) a wrapper surrounding the tobacco column and having a base permeability, the wrapper comprising:
      (1) at least one untreated area being substantially free of a permeability reducing substance and a burn rare retarding substance and
      (2) at least one discrete area comprising a circumferential band treated with a permeability reducing substance, a burn rate retarding substance and a burn rate accelerating substance, and having a lower permeability than the base permeability of the wrapper.

50. A smoking article having reduced ignition propensity comprising:
(a) a tobacco column;
(b) a wrapper surrounding the tobacco column and having a base permeability, the wrapper comprising:
(1) at least one untreated area having a porosity of at least 17 CORESTA units and
(2) at least one discrete area treated with a permeability reducing substance, a burn rate retarding substance and a burn rate accelerating substance, and having a lower porosity than the porosity of the at least one untreated area of the wrapper.

51. The smoking article according to claim 50, wherein the porosity of the at least one discrete area is less than about 6 CORESTA units.

52. The smoking article according to claim 50, wherein the porosity of the at least one discrete area is between about 3 CORESTA units and 6 CORESTA units.

53. A smoking article having reduced ignition propensity comprising:
(a) a tobacco column forming a tobacco firecone when the smoking article is ignited;
(b) a wrapper surrounding the tobacco column and having a base permeability, the wrapper comprising:
(1) at least one untreated area being substantially free of any permeability reducing substance and burn rate retarding substance and having a combustion characteristic such that as a coal of burning tobacco firecone advances along the wrapper portion the smoking article with freeburn; and
(2) at least one discrete area comprising a circumferential band treated with a permeability reducing substance, a burn rate retarding substance and a burn rate accelerating substance, and having combustion characteristic such that as a coal of the burning firecone advances along the discrete area the smoking article will self-extinguish if it placed on a substrate and will freeburn if it is freely suspended.

54. A smoking article having reduced ignition propensity comprising:
(a) a tobacco column;
(b) a swapper surrounding the tobacco column and having a base permeability, the wrapper comprising:
(1) at least one untreated area being substantially free of a permeability reducing substance and a burn rate retarding substance and
(2) at least one discrete area treated with
(i) at leant one polysaccharide selected from the group consisting of starch, modified starch, cellulose, chitosan, chitin, alginate and derivatives thereof;
(ii) at least one phosphate selected from the group consisting of monoammonium phosphate and diammonium phosphate; and
(iii) at least one burn rate accelerating substance selected from the group consisting of sodium citrate and potassium citrate.

55. A method for making a wrapper for a smoking article having reduced ignition propensity comprising:
(a) treating discrete areas of a paper having a base permeability with a composition comprising permeability reducing substance, a burn rate retarding substance and a burn rate accelerating substance and
(b) forming the paper into a wrapper for a smoking article.

56. The method according to claim 55 wherein, the composition composes starch, diammonium phosphate and a salt of citric acid.

57. The method according to claim 56, wherein the composition comprises about 14 to about 27% starch, up to about 11% alkali metal citrate salt and up to about 5% diammonium phosphate.

58. The method according to claim 56, wherein the composition comprises about 18 to about 24% starch, about 2 to about 9% alkali metal citrate salt and about 1% diammonium phosphate.

59. The method according to claim 56, wherein the composition comprises about 20 to about 22% starch, about 5 to about 9% alkali metal citrate salt and about 1% diammonium phosphate.

60. The method according to claim 56, wherein the composition comprises about 14 to about 27% starch, up to about 11% alkali metal citrate salt comprising at least one species selected from the group consisting of sodium citrate and potassium citrate, and up to about 5% diammonium phosphate.

* * * * *